United States Patent
Woodward

(10) Patent No.: US 8,987,290 B2
(45) Date of Patent: Mar. 24, 2015

(54) USE OF OPIOID FORMULATIONS IN NEEDLE-LESS DRUG DELIVERY DEVICES

(75) Inventor: Jo Woodward, Cambridge (GB)

(73) Assignee: Purdue Pharma L.P., Stamford, CT (US)

( * ) Notice: Subject to any disclaimer, the term of this patent is extended or adjusted under 35 U.S.C. 154(b) by 740 days.

(21) Appl. No.: 12/439,386

(22) PCT Filed: Aug. 29, 2007

(86) PCT No.: PCT/EP2007/058976
§ 371 (c)(1),
(2), (4) Date: Jul. 21, 2009

(87) PCT Pub. No.: WO2008/025790
PCT Pub. Date: Mar. 6, 2008

(65) Prior Publication Data
US 2010/0056554 A1  Mar. 4, 2010

(30) Foreign Application Priority Data
Aug. 29, 2006 (EP) .................... 06119722

(51) Int. Cl.
*A61M 5/30* (2006.01)
*A61K 9/00* (2006.01)

(52) U.S. Cl.
CPC ............ *A61M 5/30* (2013.01); *A61K 9/0021* (2013.01)
USPC ............ 514/282; 514/329; 514/646

(58) Field of Classification Search
None
See application file for complete search history.

(56) References Cited

U.S. PATENT DOCUMENTS

| | | | | |
|---|---|---|---|---|
| 3,735,761 | A * | 5/1973 | Hurschman et al. | 604/88 |
| 3,946,732 | A * | 3/1976 | Hurscham | 604/88 |
| 5,549,561 | A * | 8/1996 | Hjertman | 604/131 |
| 5,788,670 | A * | 8/1998 | Reinhard et al. | 604/89 |
| 5,851,198 | A | 12/1998 | Castellano et al. | |
| 6,277,384 | B1 | 8/2001 | Kaiko et al. | |
| 6,375,957 | B1 | 4/2002 | Kaiko et al. | |
| 6,406,455 | B1 * | 6/2002 | Willis et al. | 604/68 |
| 6,475,494 | B2 | 11/2002 | Kaiko et al. | |
| 6,696,066 | B2 | 2/2004 | Kaiko et al. | |
| 7,172,767 | B2 | 2/2007 | Kaiko et al. | |
| 7,419,686 | B2 | 9/2008 | Kaiko et al. | |
| 7,749,194 | B2 * | 7/2010 | Edwards et al. | 604/131 |
| 7,749,542 | B2 | 7/2010 | Kaiko et al. | |
| 7,815,598 | B2 * | 10/2010 | Hommann et al. | 604/89 |
| 8,105,631 | B2 | 1/2012 | Kaiko et al. | |
| 2002/0058673 | A1 | 5/2002 | Kaiko et al. | |
| 2004/0015126 | A1 | 1/2004 | Zierenberg et al. | |
| 2005/0245483 | A1 | 11/2005 | Brögmann et al. | |
| 2005/0245556 | A1 * | 11/2005 | Brogmann et al. | 514/282 |
| 2006/0223786 | A1 * | 10/2006 | Smith et al. | 514/114 |
| 2008/0069881 | A1 | 3/2008 | Caruso et al. | |
| 2008/0145429 | A1 | 6/2008 | Leyendecker et al. | |
| 2011/0172259 | A1 | 7/2011 | Leyendecker et al. | |
| 2012/0108621 | A1 | 5/2012 | Brögmann et al. | |
| 2012/0165359 | A1 | 6/2012 | Kaiko et al. | |
| 2012/0183612 | A1 | 7/2012 | Brögmann et al. | |
| 2012/0225901 | A1 | 9/2012 | Leyendecker et al. | |
| 2012/0252832 | A1 | 10/2012 | Caruso et al. | |
| 2013/0165418 | A1 | 6/2013 | Kaiko et al. | |
| 2013/0172382 | A1 | 7/2013 | Caruso et al. | |

FOREIGN PATENT DOCUMENTS

| | | |
|---|---|---|
| EP | 1752174 | 2/2007 |
| WO | 00/13668 | 3/2000 |
| WO | 02/47688 | 6/2002 |
| WO | 02/051470 | 7/2002 |
| WO | 03/015843 | 2/2003 |
| WO | 03/023773 | 3/2003 |
| WO | WO-03/070191 | 8/2003 |
| WO | 2004/014468 | 2/2004 |
| WO | 2005/117830 | 12/2005 |
| WO | 2007/149514 | 12/2007 |

OTHER PUBLICATIONS

Cooper et al. (Anaesthesia 2000, 55, pp. 247-250).*
Lysakowski et al. (Anesth Analg 2003, 96, pp. 215-219).*
Kost (Moderate sedation/analgesia: core competencies for practice; 2004, Elsevier Health Sciences, p. 109) 1 page.*
Kost (Moderate sedation/analgesia: core competencies for practice; 2004, Elsevier Health Sciences, p. 109).*
Baer, CL et al., "Effectiveness of a jet injection system in administering morphine and heparin to healthy adults" *Am. J. Crit. Care* 5(1): 42-48 (1996).

(Continued)

*Primary Examiner* — Ernst V Arnold
(74) *Attorney, Agent, or Firm* — Dechert LLP

(57) ABSTRACT

The present invention concerns a needle-less drug delivery device being suitable for delivering drugs through a skin surface into a human or animal body comprising a pharmaceutical composition with at least one analgesic agent preferably being an opioid. The present invention also relates to the use of at least one analgesic agent, preferably being at least one opioid in a needle-less drug delivery device being suitable for injecting medication through a skin surface into the human or animal body. Further, the invention is concerned with a method of treating breakthrough pain by injecting at least one analgesic agent preferably being an opioid into the human or animal body using a needle-less drug delivery device.

19 Claims, No Drawings

(56) References Cited

OTHER PUBLICATIONS

Burns "Ultra-low-dose opioid antagonists enhance opioid analgesia while reducing tolerance, dependence and addictive properties" *Recent Developments in Pain Research* 2005: 115-136 (2005).

Cara et al., "Safety and efficacy of intranasal ketamine for the treatment of breakthrough pain in patients with chronic pain: a randomized, double-blind, placebo-controlled, crossover study" *Pain* 108: 17-27 (2004).

Portenoy et al., "Breakthrough pain: definition, prevalence and characteristics" *Pain* 41(3): 273-281 (1990).

Portenoy et al., "Breakthrough pain: characteristics and impact in patients with cancer pain" *Pain* 81: 129-134 (1999).

Portenoy et al., "Prevalence and characteristics of breakthrough pain in opioid-treated patients with chronic noncancer pain" *J. Pain* 7: 583-591 (2006).

Ripamonti et al., "Palliative medical management" *Eur. J. Cancer. Suppl.* 3(3): 203-219 (2005).

\* cited by examiner

//www.w3.org/1999/xhtml">
USE OF OPIOID FORMULATIONS IN NEEDLE-LESS DRUG DELIVERY DEVICES This present application is a United States national application which claims priority upon PCT International Application No. PCT/EP2007/058976, filed Aug. 29, 2007, and upon European Patent Application No. EP06119722.4, filed Aug. 29, 2006.

The present invention concerns a needle-less drug delivery device being suitable for delivering drugs through a skin surface into a human or animal body comprising a pharmaceutical composition with at least one analgesic agent preferably being an opioid.

The present invention also relates to the use of at least one analgesic agent, preferably being an opioid in a needle-less drug delivery device which is suitable for injecting medication through a skin surface into the human or animal body.

Further, the invention is concerned with a method of treating breakthrough pain by injecting at least one analgesic agent preferably being an opioid into the human or animal body using a needle-less drug delivery device.

BACKGROUND OF THE INVENTION

The treatment of severe chronic pain which may be idiopathic or result from diseases such as cancer, rheumatism and arthritis is central to the treatment of these conditions. The range of pain felt by e.g., tumor patients comprises pain of the periosteum and of the bone itself as well as visceral pain and pain in soft tissues.

All chronic severe pain forms render the daily life of patients intolerable and often lead to depressive states. Successful pain therapy resulting in a lasting improvement of quality of life for the patients is therefore equally important to the success of a comprehensive therapy as is the treatment of the actual causes of the disease.

It has become accepted practice to use strong analgesics such as opioids for treating chronic severe pain for cancer patients as well as for patients which experience pain for other reasons.

Typically chronic pain patients are titrated with strong analgesics such as opioids in order to find a suitable dose range for a specific opioid such as e.g., morphine or oxycodone. Once a dosage amount being suitable to permanently control the chronic pain experience of these patients has been identified, the medication is taken on a by-the-clock-regimen which means that a certain dose will be taken e.g., every 8 hours, every 12 hours or only once a day. Such patients which without pain treatment would suffer from chronic pain sensation are typically designated as patients with a controlled background pain.

In order to achieve a constant control of background pain, patients will usually administer so-called controlled release or sustained release preparations of the analgesic in question. Sustained release preparations particularly of opioids are well-known in e.g., in the form of the tablets "MST-Continus", "Palladon" and "Oxygesic" (all marketed by Mundipharma GmbH, Germany). These sustained release dosage forms are characterized in that they release the active agent over a prolonged period of time which allows the frequency of administration of these preparations to be reduced. This in turn has a number of important advantages for the patient because the patient for example can sleep through a constant period of 6 to 8 hours. Furthermore, the reduced frequency of administration often leads to increased patient compliance with medication.

Even though a lot of cancer patients are nowadays treated with opioids efficiently and can be considered to have controlled background pain, they experience from time to time a transitory increase in pain to greater than the usual moderate intensity.

This flare-up of moderate to severe pain that "breaks through" despite a by-the-clock analgesic regimen for treatment of chronic pain is typically described at breakthrough pain (BTP). The term breakthrough pain has become accepted in the lexicon of chronic pain treatment specialists and thus refers generally to a transitory exacerbation of pain that occurs on a background of otherwise stable controlled pain in a patient receiving analgesic therapy (see e.g., Portenoy et al (1990), *Pain*, 41:273-281, Cara et al (2004), *Pain*, 108:17-27, Portenoy et al (1999), *Pain*, 81:129-134 and Portenoy et al (2006) *The Journal of Pain*, 7(8):583-591). The phenomenon of breakthrough pain has also been labelled as "incident pain" and "episodic pain".

In studies of cancer populations, 50 to 90% of patients with chronic pain experience breakthrough pain attacks which have also been reported in opioid-treated patients with chronic non-cancer pain (see Portenoy et al (2006), *The Journal of Pain*, 7(8):583-591).

Thus, even though treatment of pain, regardless of its origin, with strong analgesics as opioids nowadays does not encounter the same prejudices by medical practitioners as in the past, a well-titrated patient which is on a continuous opioid dosage regimen may still suffer from annoying and painful attacks. Clearly there is a strong need to account for the breakthrough pain phenomenon and different attempts have been made in the prior art to render the life of these patients which suffer from sudden pain attacks more comfortable.

For treating breakthrough pain a patient will typically receive an additional amount of a strong analgesic such as the opioid which he constantly takes for controlling the background pain.

As breakthrough pain attacks occur usually suddenly and need to be treated on a short time scale, these additional analgesic dosage amounts will usually be provided in the form of a fast acting preparation. In case of opioids one may therefore administer the additional dosage either parenteral, which would give an immediate onset of action, or alternatively administer oral immediate release preparations of opioids such as e.g., morphine and oxycodone.

Oral immediate release dosage forms may take the form of liquids or immediate release tablets.

In view of the recognition that breakthrough pain represents a significant clinical problem, such "rescue medication" has become widely accepted for treating pain.

However, as short acting opioid formulations are typically used for treating breakthrough pain attacks on an "as needed" basis in patients which already take a fixed scheduled opioid regimen, one has to take care that a patient is not overdosed. Additionally short acting opioid formulations such as liquids that are either to be taken by the oral route or administered parenterally, are notoriously prone to abuse by individuals that do not attempt to take the medication for treating pain but rather will try to isolate the opioids thereof and to use them for illicit recreational purposes.

Given the possibility that exposure to short-acting opioid formulations might increase the risk of abuse among the sub-population pre-deposed to abuse or addiction it is prudent to implement rescue dosing on a case by case basis after a careful assessment of risks and benefits. This typically leads to the situation that patients suffering form breakthrough pain receive the necessary short acting medication only under supervision of a medical practitioner which, of course severely impairs the freedom of such patients to move and to take the required medicine at any location and point in time. Parenteral administration of short acting opioids also severely suffers from the low acceptance of administering a medication by a needle device.

Moreover, it was found that patients on oral dosing find that the onset of action of an oral dose is sometimes too slow to experience rescue and therefore typically better results in treating breakthrough pain attacks are achieved with parenteral "rescue" medication.

Thus, there is a strong need in the art to provide a pharmaceutical composition that allows treatment of breakthrough pain and which can be taken by a patient as needed without supervision of medical practitioners at any time. At the same time these pharmaceutical compositions should be less prone to abuse as are the fast acting opioid formulations that are commonly used for treating breakthrough pain attacks.

OBJECT AND SUMMARY OF THE INVENTION

It is an object of the present invention to provide a medication that can be used as rescue medication for treating breakthrough pain. It is also an object of the present invention to provide a drug delivery device which allows to deliver a medication being suitable for treating breakthrough pain which can be administered by the patients themselves on demand and which is less prone to abuse as are the short-acting opioid formulations that are commonly used for treating breakthrough pain attacks.

One embodiment of the present invention thus relates to a needle-less drug delivery device suitable for injecting a pharmaceutical composition through a skin surface into a human or animal body, the needle-less drug delivery device comprising:
  (a) a housing;
  (b) a means of generating a force capable of pushing a pharmaceutical composition from a packaging into a human or animal body through a skin surface;
  (c) a means for transmitting said force to push the pharmaceutical composition from a packaging into a human or animal body through a skin surface;
  (d) a means for triggering the device;
  (e) and a pharmaceutical composition comprising at least one analgesic agent.

Said at least one analgesic agent may be present in the pharmaceutical composition in the form of a solution, a solid, a dispersion or a suspension.

Opioids form a preferred subgroup of analgesics with the group consisting of tramadol, dihydrocodeine, oxycodone, morphine, hydromorphone, oxymorphone, nalbuphine, etorphine, dihydroetorphine, fentanyl, sulfentanil, remifentanil, and buprenorphine or pharmaceutically acceptable salts thereof being preferred.

Particularly preferred opioids are hydromorphone and oxycodone with their hydrochloride salts being also particularly preferred.

The present invention also relates to the use of at least one analgesic in a needle-less drug delivery device which is suitable for injecting a pharmaceutical composition through a skin surface into a human or animal body.

Yet another embodiment of the present invention relates to the use of at least one analgesic in the manufacture of a medicament for treating breakthrough pain wherein said at least one analgesic is administered through a skin surface into a human or animal body using a needle-less drug delivery device.

The present invention is also concerned with the use of a needle-less drug delivery device which is suitable to inject a medication through a skin surface into the human or animal body for manufacturing a medicament for treating breakthrough pain. In the latter case the drug delivery device will of course comprise a pharmaceutical composition comprising at least one analgesic agent.

In all of the aforementioned cases the at least one analgesic agent may be present in the form of a solid, liquid, dispersion or suspension.

It is also preferred to use opioids as the at least one analgesic with the group of opioids consisting of tramadol, dihydrocodeine, oxycodone, morphine, hydromorphone, oxymorphone, nalbuphine, etorphine, dihydroetorphine, fentanyl, sulfentanil, remifentanil, and buprenorphine being preferred. Particularly preferred opioids are hydromorphone and oxycodone and their hydrochloride salts.

Yet another embodiment of the present invention relates to a method of treating breakthrough pain in a patient in need thereof wherein at least one analgesic agent is administered to the patient using a needle-less drug delivery device suitable for injecting medication through a skin surface into a human or animal body.

Again, the analgesic agent may be present in the form of a solution, solid, dispersion or suspension. Opioids such as the group consisting of tramadol, dihydrocodeine, oxycodone, morphine, hydromorphone, oxymorphone, nalbuphine, etorphine, dihydroetorphine, fentanyl, sulfentanil, remifentanil, and buprenorphine will be preferred, with a particular focus on hydromorphone, oxycodone and their hydrochloride salts.

DETAILED DESCRIPTION OF THE INVENTION

In the context of the present invention the term "breakthrough pain" refers to a transitory increase in pain to greater than moderate intensity which occurs on a baseline pain of moderate intensity or less.

"Baseline pain" is the pain that is reported by a patient as the average pain intensity experience for 12 or more hours with the patient being on an opioid regimen for treating chronic pain.

Pain intensities of baseline pain will typically be determined using common methods such as a numerical analogue scale test (NAS). Determination of breakthrough pain attacks and baseline pain has been described in detail in the aforementioned publication of Portenoy (see particularly Portenoy et al. (1999) (*The Journal of Pain* 7(8):583-591) and Portenoy et al (1999) *Pain* 81:129-134). The definitions of breakthrough pain and controlled baseline pain as given in these two publications are incorporated by reference herewith. Thus, the designation of controlled baseline pain will require that two criteria are met. First the patients will have to answer the question "Does your pain currently have a component you would describe as "constant" or "almost constant" or would be constant or almost if not for the treatment you are receiving" must be answered in the affirmative. Second such patients must be required to be treated by an opioid regimen that is consistent with relatively good pain control. The person skilled in the art will of course know how to determine control baseline pain on the basis of the information provided in the two references. Breakthrough pain will then be identified as a flair of pain which is experienced by the patient above the level of controlled baseline pain.

Pain intensity may thus be assessed using e.g., a 5-point categorical scale with the items "none", "slight", "moderate", "severe" and "excruciating". By definition a patient will experience a breakthrough pain attack if this attack has been rated by the patient as either severe or excruciating.

As mentioned above one embodiment of the present invention refers to a needle-less drug delivery device suitable for injecting a pharmaceutical composition through a skin surface into a human or animal body, the needle-less drug delivery device comprising:

(a) a housing;

(b) a means of generating a force capable of pushing a pharmaceutical composition from a packaging into a human or animal body through a skin surface;

(c) a means for transmitting said force to push the pharmaceutical composition from a packaging into a human or animal body through a skin surface;

(d) a means for triggering the device;

(e) a pharmaceutical composition comprising at least one analgesic agent.

Thus, the present invention relates in one embodiment to needle-less injector devices as described in the prior art with the difference being that the injector devices are loaded with a pharmaceutical composition comprising an analgesic, preferably being an opioid.

The person skilled in the art is of course clearly aware that different needle-less pen injectors as described in the prior art may be used. The person skilled in the art is also aware that these different needle-less pen injector devices as they are described in the prior art for e.g., insulin or hormones such as human growth factor and follicle stimulating hormone differ as to their mechanical elements and construction.

However, while these differences in construction may impose certain requirements on the type of pharmaceutical composition that can be used within the drug delivery devices, the person skilled in the art will understand that these constructional differences of the prior art needle-less injector devices do not matter with respect to the present invention which lies in the surprising realization that such needle-less pen injectors can be ideally used to treat breakthrough pain by administering strong analgesics such as preferably opioids.

Therefore, one may use a needle-less injector device which contains pre-filled and pre-measured dosages of analgesics which are propelled from the injector by compressed inert gas. The pressure will be sufficient to pierce the liquid medication through the skin surface of the patient.

Thus, one may use for the purposes of the present invention for example the needle-less injector device described in U.S. Pat. No. 5,851,198 which is incorporated by reference herewith.

One may also use the pen injector devices described in WO 03/015843 A2 which is also incorporated by reference in its entirety.

In a preferred embodiment one may use the pen injector devices as described in WO 03/023773 A1 and WO 2004/014468 A1 both in the name of Caretek Medical Ltd. both of which are incorporated by reference herein as regards the needle-less drug delivery devices described therein.

The person skilled in the art will of course know that there are various means of generating a force capable of pushing a medication from a packaging into a human or animal body through a skin surface. These means of generating a force may e.g., comprise compressed gases or spring technology.

Similarly the means of transmitting said force are also well-known to the person skilled in the art as are the means for triggering the device.

While some of the aforementioned drug delivery devices rely on a technology which delivers the drug by creating a very fine, high velocity liquid jet that creates its own hole through the skin, the technology described in WO 03/023773 A1 and WO 2004/014668 A1 relates on an alternative technology in which a pioneer projectile is first forced through the skin followed by the medication which ensures an efficient transfer of the active agent through the skin surface. One of the advantages of the technologies described in WO 03/023773 A1 and WO 2004/014468 A1 is that one may use a pharmaceutical composition that comprises the active agent in solid state, liquid state, in a semi-solid-state, as a paste or in liquid states of different viscosity. Thus, the devices described in WO 03/023773 A1 and WO 2004/014468 A1 allow to deliver analgesics and particularly opioids for treating breakthrough pain in the form of a liquid which may be contained by a membrane, as a liquid with a viscosity of at least 5000 centipoises, as a semi-solid, as a paste having a soft malleable consistency, as a gel being a liquid dispersed in a solid or in the solid state.

The advantages of using a needle-less drug delivery device comprising at least analgesic being preferably an opioid for treating breakthrough pain include inter alia that a patient may use this device and will not have the same dislike as for classical needle technology. This will significantly increase ease of administration and at the same time decrease skin irritations as they may occur using classical needle technology.

Furthermore, as the active agents in this case preferably being opioids are administered through the skin surface, the active agent is systemically resorbed on a short time scale providing the fast onset of action which is required for treating breakthrough pain efficiently.

Furthermore, the pen injector devices are much less prone to abuse. For example, a single-use pen injector may comprise the dosage of the analgesic already incorporated in a ready-to-use injector which could make it much harder to isolate the analgetic formulation from the pen injector than from e.g., the prior art liquid formulations that have to be taken orally. If on the other side the formulation is contained within a replaceable container that is to be inserted into the pen injector, the container may be designed to make illicit isolation of the analgetic formulation very difficult. The person skilled in the art is of course clearly aware that it is possible to construct the needle-less pen injector device such that it becomes difficult to isolate an opioid formulation from a needle-less drug delivery device. For example, the opioid formulation may be placed within the container in separation form another formulation comprising e.g., an opioid antagonist in relevant amounts. The two formulations may be placed in the container of the needle-less pen injector such that if one tries to disassemble the container, both formulations will contact each other which will prevent any parenteral abuse of the formulations (so called two chamber approach).

Depending on the constructive elements, the needle-less pen injector for delivering analgesics and particularly opioids in order to treat breakthrough pain attacks may be configured to allow for administration of a single dose only or repeated administration. Thus, the needle-less pen injector devices may be for single use or multiple uses and be e.g., a throw away or reusable injector. The different constructive elements which may be necessary to make a needle-less pen injector device either a single or multiple use injector are well known to the person skilled in the art from other pen injector devices such as those which are used for insulin or growth hormone application.

Depending on the type of needle-less pen injector device, the dosage amount of the analgesic and preferably the opioid may be pre-fixed or adjustable. A pen injector device with an adjustable dosage amount of e.g., opioid will have the advantage that a responsible patient could administer the dosage depending on the severity of the pain attack. On the other side, a pre-fixed dosage amount will additionally reduce the abuse potential of the analgesic compositions being contained within the needle-less pen injector devices. Other advantages and embodiments of the needle-less pen injector devices comprising pharmaceutical compositions with at least one analgesic preferably being an opioid will be obvious to the person skilled in the art.

As regards the pharmaceutical composition comprising the at least one analgesic which preferably is an opioid, the person skilled in the art is, of course, clearly aware that these formulations may take different forms and comprise optionally different pharmaceutically acceptable excipients where necessary.

When designing the formulation of the at least analgesic being preferably at least one opioid for the needle-less pen injector device as described, two aspects will be mainly regarded by the person skilled in the art.

As the purpose of the present invention is to use the afore-described needle-less pen injector devices for treating breakthrough pain attacks, the pharmaceutical compositions contained within the injector will have to ensure that the active agent is capable of exerting a fast onset of action. As the pharmaceutical compositions comprising the at least one analgesic agent preferably being an opioid will be administered by injection through the skin surface, the onset of action typically occurs earlier compared to a situation where the same formulation is orally administered.

However, the person skilled in the art will, of course, make sure that, if the pharmaceutically active agent is e.g., administered in liquid form by injection, that the liquid will provide the characteristics of an immediate release formulation. Thus, a person skilled in the art having the treatment of breakthrough pain in his mind will, of course, avoid the use of excipients and components that are known to significantly retard the release and resorption of the active agent by the human or animal body once the active agent has been injected. The second aspect that will be considered by the person skilled in the art when developing a pharmaceutical composition of the active agent will be that this composition is compatible with the mechanical requirements of the needle-less pen injector that is to be used.

As already set out above a person skilled in the art may consider a pharmaceutical composition which comprises the active agent in solid, liquid, dispersed or suspended form.

Currently it is preferred to use a liquid formulation of the analgesic active agent preferably being an opioid. In its most simple embodiment such a liquid formulation may comprise e.g., morphine or oxycodone in a saline solution at physiological pH values. However, the person skilled in the art may also consider to use inject the active agent in a solid state. In this context it will be clear that the finer the size of the solid particles of the active agents is, the faster the active will be systemically resorbed by the patient.

As regards the analgesics and particularly the opioids to be used the person skilled in the art will consider use of the free base as well as pharmaceutically acceptable salts thereof or derivatives which are known to be also therapeutically active and pharmaceutically acceptable. If in the contest of this invention an opioid is mentioned, this always refers to the free base as well as to the pharmaceutically acceptable salts or the afore-mentioned derivatives.

If, for example, oxycodone is mentioned, this also comprises, besides the free base, their hydrochloride, sulfate, bisulfate, tartrate, nitrate, citrate, bitartrate, phosphate, malate, maleate, hydrobromide, hydrojodide, fumarate, succinate and the like.

In case of hydromorphone and oxycodone, the hydrochloride salt will be preferred.

As mentioned above opioids are preferred for treating breakthrough pain and these opioids may include morphine, oxycodone, hydromorphone, propoxyphene, nicomorphine, dihydrocodeine, diamorphine, papaveretum, codeine, ethylmorphine, phenylpiperidine and derivates thereof, methadone, dextropropoxyphene, buprenorphine, pentazocine, tilidine, tramadol, hydrocodone. Further examples for useable opioid analgesics according to the invention are buprenorphine, meperidine, oxymorphone, alphaprodine, anileridine, dextromoramide, metopone, levorphanol, phenazocine, etoheptazine, propiram, profadol, phenampromide, thiambuten, pholcodeine, codeine, dihydrocodeinon, fentanyl, 3-trans-dimethylamino-4-phenyl-4-trans-carbethoxy-Λ'-cyclohexen, 3-dimethylamino-0-(4-methoxyphenyl-carbamoyl)-propiophenone oxime, (−)β-2'-hydroxy-2,9-dimethyl-5-phenyl-6,7-benzomorphane, (−)2'-hydroxy-2-(3-methyl-2-butenyl)-9-methyl-5-phenyl-6,7-benzomorphane, pirinitramide, (−)α-5,9-diethyl-2' hydroxy-2-methyl-6,7-benzomorphane, ethyl 1-(2-dimethylaminoethyl)-4,5,6,7-tetrahydro-3-methyl-4-oxo-6-phenyl-indol-2-carboxylate, 1-benzoylmethyl-2,3-dimethyl-3-(m-hydroxy-phenyl)-piperidine, N-allyl-7α(1-R-hydroxy-1-methylbutyl)-6,14-endo-ethanotetrahydronororipavine, (−)2'-hydroxy-2-methyl-6,7-benzomorphane, noracylmethadol, phenoperidine, α-dl-methadol, α-1-methadol, β-dl-acetylmethadol, α-1-acetylmethadol and β-1-acetylmethadol.

Particularly preferred is the group of opioids comprising tramadol, dihydrocodeine, oxycodone, morphine, hydromorphone, oxymorphone, nalbuphine, etorphine, dihydroetorphine, fentanyl, sulfentanil, remifentanil, and buprenorphine or the pharmaceutically acceptable salts thereof.

A particularly preferred embodiment of the present invention relates to the use of the opioids oxycodone or hydromorphone and preferably of their hydrochloride salts for treating breakthrough pain attacks by implementing an oxycodone or hydromorphone formulation into a needle-less drug delivery device as described above and injecting it through the skin into the human or animal body.

The dosage to be administered for treating breakthrough pain attacks efficiently will have to be determined for each opioid separately. However, it is preferred to use between approximately 10% to 30% of the dosage amount that a patient with controlled baseline pain which is adjusted to an opioid regimen will receive during a day by oral administration. Further preferred is to use approximately 10 to 20% and approximately 15% of the dosage amount that a patient with controlled baseline pain receives via oral administration over a day. The person skilled in the art is also aware that, particularly if a patient is treated with a high dosage of opioids, 10%-15% of the daily dosage taken per os will be sufficient.

The term "approximately" indicates a deviation from the specified value of 10% and preferably of 5%.

The person skilled in the art is clearly aware that this calculated dosage refers to a dosage amount for treating breakthrough pain by administration of an analgesic formulation per os. As according to the invention, the analgesic formulation will be injected subcutaneously, the person skilled in the art will typically divide the dosage for treating breakthrough pain by per os administration by a factor that is specific for each opioid. This factor is typically based on known per os:intravenous dosage amounts and reflects the fact that a first-pass effect may not occur upon parenteral administration for a lot of opioids or other analgesics. No such additional factors are usually necessary if the reference amount of the opioid (analgesic) refers to parenteral administration per day for achieving controlled background pain.

In case of morphine this factor will e.g., be approximately 3, in case of hydromorphone this factor will e.g., be approximately 5, in case of oxycodone this factor will be approximately 2, in case of tramadol this factor will e.g., be approximately 1, in case of codeine this factor will e.g., be approximately 5.

It is understood that the above per os:intravenous ratios are guides to define the dose required. Inter-patient variability requires that each patient will be carefully titrated to the appropriate dose.

In case of morphine, the daily dosage administered per os typically ranges from approximately 30 mg to approximately 1000 mg per day per os. The dosage amount of morphine to be administered for treating breakthrough pain attacks per os will therefore be in the range of approximately 3-9 mg to approximately 100 to 300 mg. A preferred range for a morphine per os ratio for treating break through pain will be approximately 3-9 mg to approximately 40 mg to 120 mg. The dosage to be administered for treating breakthrough pain attacks subcutaneously will correspondingly be in the range approximately 1-3 mg to approximately 33 to 50 mg and preferably in the range of approximately 1 to 3 mg to approximately 13-40 mg.

For hydromorphone it is known that the typical daily dosage in a steady state ranges from approximately 2 mg to approximately 400 mg. The dosage range treating breakthrough pain attacks per os will therefore range from approximately 0.2-0.6 mg to approximately 40-120 mg and preferably from approximately 0.4-1.2 mg to approximately 6.4-19.2 mg. The dosage to be administered for treating breakthrough pain attacks subcutaneously will correspondingly be in the range approximately 0.04-0.12 mg to approximately 8 to 20 mg and preferably in the range of approximately 0.08-0.24 mg to approximately 1.3-5.9 mg.

For tramadol typical dosage amount range from approximately 50 mg to approximately 600 mg and preferably from approximately 50 mg to approximately 400 mg per day during a steady state application. In a typical breakthrough pain treatment scenario, one will therefore administer per os or subcutaneously between approximately 5-15 mg to approximately 60-180 mg tramadol and preferably between approximately 5-15 mg to approximately 40-120 mg.

Fentanyl is typically administered in an amount of 600 µg to 2.4 mg per day either intravenously or transdermally. Therefore the dosage for treating breakthrough pain attacks subcutaneously will be between approximately 60-180 µg to approximately 0.24 mg to 0.72 mg.

Codeine is typically administered subcutaneously in an amount of up to 240 mg. Therefore the dosage for treating breakthrough pain attacks subcutaneously will be between up to approximately 24-72 mg.

Dihydrocodeine is typically administered intravenously in an amount of up to 320 mg. Therefore the dosage for treating breakthrough pain attacks subcutaneously will be between up to approximately 32-96 mg.

In case of oxycodone the typical daily dosage amount ranges from approximately 5 mg to approximately 800 mg per day. For treating breakthrough pain attacks one will therefore typically use per os between approximately 0.5-1.5 mg to approximately 80 to 240 mg oxycodone and preferably between approximately 1-3 mg to approximately 16-48 mg. The dosage to be administered for treating breakthrough pain attacks subcutaneously will correspondingly be in the range of approximately 0.25-0.75 mg to approximately 40 to 120 mg and preferably of approximately 0.5-1.5 mg to approximately 8-24 mg.

All of the aforementioned preferably refer to the respective hydrochloride salts.

It is understood by the person skilled in the art that the amount of opioid to be administered to efficiently treat a breakthrough pain attack will thus depend on the amount that is used on a daily basis to achieve baseline pain control. Thus, if a patient is to be treated for breakthrough pain attacks who is on e.g., 32 mg dosage amount of hydromorphone per day per os, a typical amount considered for treating the breakthrough pain attacks will be between e.g., 3.2 and 9.6 mg per os or between 1 and 3 mg subcutaneously or intravenously. If, another patient who also receives a hydromorphone treatment is on 8 mg per day, the necessary amount to treat breakthrough pain attacks efficiently may be e.g., in the range of 0.8 to 2.4 mg per os or between 0.2 and 0.5 mg IV.

As regards the precise amount of opioid that will be needed to treat efficiently a breakthrough pain attack, a person skilled in the art will consider various factors. As has been set out above, one factor will be the total daily dosage amount which is taken by a patient in order to achieve controlled baseline pain. This total amount will be typically the dosage amount that is taken over the period of 24 hours orally and 10 to 30% of that dosage will be a good first estimate for treating breakthrough pain per os. However, within that range of 10 to 30% the specific amount may depend on the frequency and severity of breakthrough pain attacks and for subcutaneous administration by a needle-less drug delivery device for subcutaneous injection, the amount will often be less.

The person skilled in the art is well-acquainted with measuring both the frequency and intensity of breakthrough pain attacks in clinical trials. The design of such clinical trials is e.g., described in detail e.g., in the aforementioned publication by Portenoy et al (*The Journal of Pain* (2006) 7(8):583-591). From this publication it can be seen that in case of non-cancer patients with chronic controlled pain the typical occurrence of breakthrough pain attacks will be approximately 2.4 attacks per day in most patients. Furthermore, table 2 of this publication gives a good overview on the different pain symptoms which may be classified as breakthrough pain attacks. The person skilled in the art will also be familiar with the type of clinical trials and the design of such clinical trials in order to determine controlled baseline pain and breakthrough pain attacks. Typically, a person skilled in the art will design a trial for a group of approximately 15 to 100 people. However, a group of 20 patients may be sufficient. These patients are enrolled in such a trial on the basis of certain inclusion and exclusion criteria which follow recommendations of the regulatory authorities such as the FDA and EMEA. A good overview on typical inclusion criteria such as age, sex, raise, body weight, physical condition, type and frequency of medication etc. can be found in the aforementioned references.

It has set out before that one of the advantages to use analgesic and particularly opioid formulations in a needle-less drug delivery device is that abuse of the opioid formulations is less likely given that it is harder to isolate the opioid formulations from such a device.

In order to further decrease the abuse potential of such formulations, one may consider to additionally incorporate pharmaceutical compositions into the pen injector system and/or the container comprising opioid antagonists such as naltrexone, naloxone, nalmefene, nalorphine, nalbuphine, naloxoneazinen, methylnaltrexone, ketylcyclazocine, norbinaltorphimine, naltrindol, 6-β-naloxol and 6-β-naltrexol or the pharmaceutically acceptable salts thereof following the afore-mentioned two-chamber approach. Thus, the opioid and antagonist formulation would be separated and only come into contact if one was to illicitly try to disassemble the pen injector and/or to break the container in order to isolate the opioid formulation. This approach would prevent isolation of the opioids without the antagonist and thus parenteral abuse.

Especially preferred antagonists comprise naltrexone, nalmefene and naloxone. Specifically preferred as an antagonist is naloxone and its hydrochloride salt.

The person skilled in the art is clearly aware that the opioid formulation which is to be administered by the pen injector should usually not comprise opioid antagonists in relevant amount as this would induce withdrawal symptoms instead of efficient breakthrough pain treatment.

However, in one embodiment one may consider to incorporate pharmaceutical compositions into the pen injector system and/or the container comprising opioids and particularly the opioids tramadol, dihydrocodeine, oxycodone, morphine, hydromorphone, oxymorphone, nalbuphine, etorphine, dihydroetorphine, fentanyl, sulfentanil, remifentanil, and buprenorphine together with opioid antagonists such as naltrexone, naloxone, nalmefene, nalorphine, nalbuphine (ist ein μ-Rezeptor-Antagonist und k-Rezeptor-Agonist), naloxoneazinen, methylnaltrexone, ketylcyclazocine, norbinaltorphimine, naltrindol, 6-β-naloxol and 6-β-naltrexol or the pharmaceutically acceptable salts thereof in one formulation.

This may be considered if very low dosage amounts of the antagonist are included in the formulation, namely only $10^5$ to $10^9$ less antagonist than the opioid agonist. Such very low antagonist dosages would not induce withdrawal symptoms or affect pain treatment efficacy, but may reduce tolerance development and/or hyperalgesia (Burns et al. (2005) *Recent developments in pain research:* 115-136). In this context, the peripheral acting antagonists alvimopan and methylnaltrexone may be particularly be preferred as they should also allow to counteract constipation and vomiting. Moreover, if peripherally acting opioid antagonists such as methylnaltrexone or alvimopan are chosen or alternatively peptide-based opioid receptor antagonists, hardly any reduction in analgesic efficacy will be seen.

As described above one object of the present invention is to use the aforementioned pharmaceutical compositions of analgesics and particularly preferably the opioid formulations of tramadol, dihydrocodeine, oxycodone, morphine, hydromorphone, oxymorphone, nalbuphine, etorphine, dihydroetorphine, fentanyl, sulfentanil, remifentanil, and buprenorphine in the above-indicated amounts in a needle-less drug delivery device which is suitable for injecting a pharmaceutical composition through a skin surface into the human or animal body. Such a needle-less injector device may then be used to treat breakthrough pain attacks.

Therefore, one embodiment of the present invention also relates to the use of at least one analgesic agent and preferably the aforementioned preferred opioids in the above-indicated amounts in the manufacture of a medicament for treating breakthrough pain wherein the at least one analgesic and preferably the aforementioned preferred opioids in the indicated amounts are administered through a skin surface into a human or animal body using a needle-less drug delivery device which is suitable for injecting medication through a skin surface into a human or animal body.

The application of particularly opioids such as tramadol, dihydrocodeine, oxycodone, morphine, hydromorphone, oxymorphone, nalbuphine, etorphine, dihydroetorphine, fentanyl, sulfentanil, remifentanil, and buprenorphine in the above-indicated amounts using needle-less pen injector devices are clear.

First of all, the breakthrough pain attacks are not treated by oral formulations which, as described above, may not provide a sufficiently fast onset of action. At the same time, the drawback of parenteral application which results from the use of needle technology is avoided. Thus, due to the ease of use of such needle-less pen injector devices, the patient may take the medication with it and inject it at any time and location when and where necessary. Furthermore, if the pen injector device allows for multiple use or for adjustment of dosage, administration of the medication can be fine-tuned to the frequency and severity of pain attacks. On the other side if the frequency and severity of pain attacks which often is known (see the above publications by Portenoy et al.), a patient may use a single use throw away needle-free pen injector devices comprising the opioid formulations and administer a pre-described dose.

The person skilled in the art will be aware that depending on whether such a formulation will be administered multiple times or not it may be necessary and advisable to include a preservative such as for example benzalkonium chloride or other well-known preservatives that are commonly used in multiple pen injectors such as benzyl chloride.

In addition to the aforementioned embodiments, the present invention also concerns a method of treating breakthrough pain in a patient in need thereof wherein at least one analgesic and preferably the above-described opioid formulations are administered to the patient using a needle-less drug delivery device which is suitable for injecting medication through a skin surface into a human or animal body.

It is emphasised for all of the above-described embodiments of the invention the use of the opioid analgesics hydromorphone and oxycodone is preferred. It is also understood that the use of liquid opioid formulations in the needle-less drug delivery device will be preferred at the moment.

While the invention has been described above with respect to some of its preferred embodiments, this has not been done in any way to limit the scope of the invention. The core of the invention lies in the recognition that it is possible and recommendable to treat breakthrough pain attacks as defined above by administering opioids through a needle-free drug delivery device through the skin surface into the human or animal body.

The invention claimed is:

1. A needleless drug delivery device suitable for injecting a pharmaceutical composition through a skin surface into a human or animal being, the needleless drug delivery device comprising:
   a container comprising two chambers separating a first pharmaceutical composition in one chamber from a second pharmaceutical composition in the other chamber;
   a means for generating a force capable of pushing the first pharmaceutical composition and not the second pharmaceutical composition from the container into a human or animal body through a skin surface;
   a means for transmitting said force to push the first pharmaceutical composition and not the second pharmaceutical composition from the container into a human or animal body through a skin surface; and
   a means for triggering said force;
   wherein the first pharmaceutical composition comprises at least one opioid and the second pharmaceutical composition comprises an opioid antagonist.

2. The device according to claim 1, wherein said device is suitable for multiple use.

3. The device according to claim 1, wherein said first pharmaceutical composition comprises said at least one opioid as a solution, a solid, a dispersion, or a suspension.

4. The device according to claim 1, wherein said opioid is selected from the group consisting of tramadol, dihydrocodeine, oxycodone, morphine, hydromorphone, oxymorphone, nalbuphine, etorphine, dihydroetorphine, fentanyl, sufentanil, remifentanil, and buprenorphine and pharmaceutically acceptable salts thereof.

5. The device according to claim 4, wherein said opioid is selected from the group consisting of:
   between approximately 3 mg to 30 mg of morphine or the equivalent amount of a pharmaceutically acceptable salt thereof;
   between approximately 0.75 mg to 40 mg of oxycodone or the equivalent amount of a pharmaceutically acceptable salt thereof;
   between approximately 0.08 mg to 8 mg of hydromorphone or the equivalent amount of a pharmaceutically acceptable salt thereof;
   between approximately 3 mg to 45 mg of codeine or the equivalent amount of a pharmaceutically acceptable salt thereof; and
   between approximately 15 mg to 60 mg of tramadol or the equivalent amount of a pharmaceutically acceptable salt thereof.

6. The device according to claim 1, wherein said opioid antagonist is selected from the group consisting of naloxone, naltrexone, nalmefene, nalorphine, nalbuphine, naloxoneazinen, methylnaltrexone, ketylcyclazacine, norbinaltorphimine, naltrindol, 6-β-naloxol, and 6-β-naltrexol and pharmaceutically acceptable salts thereof.

7. The device according to claim 4, wherein said opioid is selected from the group consisting of hydromorphone and oxycodone and pharmaceutically acceptable salts thereof.

8. The device according to claim 7, wherein said opioid is selected from the group consisting of hydromorphone hydrochloride and oxycodone hydrochloride.

9. The device according to claim 6, wherein said opioid antagonist is selected from the group consisting of naloxone, naltrexone, and nalmefene and pharmaceutically acceptable salts thereof.

10. The device according to claim 1, wherein said device is suitable for single use only.

11. The device according to claim 1, wherein the container is a replaceable container.

12. A method of treating a human or animal for pain comprising administering at least one opioid through a skin surface into the body of the human or animal using a needleless drug delivery device according to claim 1.

13. The method according to claim 12, wherein said pain is breakthrough pain.

14. The method according to claim 12, wherein said device is suitable for multiple use.

15. The method according to claim 12, wherein said first pharmaceutical composition comprises said at least one opioid as a solution, a solid, a dispersion or a suspension.

16. The method according to claim 12, wherein said opioid is selected from the group consisting of tramadol, dihydrocodeine, oxycodone, morphine, hydromorphone, oxymorphone, nalbuphine, etorphine, dihydroetorphine, fentanyl, sufentanil, remifentanil, and buprenorphine and pharmaceutically acceptable salts thereof.

17. The method according to claim 16, wherein
   morphine is administered subcutaneously in an amount of between approximately 3 mg to 30 mg or in an equivalent amount of a pharmaceutically acceptable salt thereof,
   oxycodone is administered subcutaneously in an amount of between approximately 0.75 mg to 40 mg or in an equivalent amount of a pharmaceutically acceptable salt thereof,
   hydromorphone is administered subcutaneously in an amount of between approximately 0.08 mg to 8 mg or in an equivalent amount of a pharmaceutically acceptable salt thereof,
   codeine is administered subcutaneously in an amount of between approximately 3 mg to 45 mg or in an equivalent amount of a pharmaceutically acceptable salt thereof, or
   tramadol is administered subcutaneously in an amount of between approximately 15 mg to 60 mg or in an equivalent amount of a pharmaceutically acceptable salt thereof.

18. The method according to claim 16, wherein said opioid is selected from the group consisting of hydromorphone and oxycodone and pharmaceutically acceptable salts thereof.

19. The method according to claim 18, wherein said opioid is selected from the group consisting of hydromorphone hydrochloride and oxycodone hydrochloride.

* * * * *